United States Patent [19]
Grabenkort

[11] Patent Number: 5,807,345
[45] Date of Patent: Sep. 15, 1998

[54] LUER CAP FOR TERMINALLY STERILIZED SYRINGE

[75] Inventor: Richard W. Grabenkort, Barrington, Ill.

[73] Assignee: Abbott Laboratories, Abbott Park, Ill.

[21] Appl. No.: 884,314

[22] Filed: Jun. 27, 1997

Related U.S. Application Data

[63] Continuation of Ser. No. 496,990, Jun. 30, 1995, abandoned.

[51] Int. Cl.⁶ ........................................................ A61M 5/32
[52] U.S. Cl. ........................... 604/199; 604/192; 604/256; 215/211
[58] Field of Search ..................................... 604/111, 192, 604/199, 206, 241–243, 256, 283, 905, 240; 215/200, 201, 202, 208, 211, 214, 217, 218, 219, 246, 252, 318, 320

[56] References Cited

U.S. PATENT DOCUMENTS

| | | | |
|---|---|---|---|
| 2,677,374 | 5/1954 | Burnside | 604/199 |
| 2,723,041 | 11/1955 | Hart-Still | 215/296 X |
| 2,812,763 | 11/1957 | Ferguson | 604/199 |
| 2,935,219 | 5/1960 | Smith | 215/21 |
| 3,716,160 | 2/1973 | Thomas | 215/211 X |
| 3,733,771 | 5/1973 | Megowen | 215/320 X |
| 3,991,895 | 11/1976 | Thornton | 215/211 |
| 3,994,412 | 11/1976 | Difiglio | 220/266 |
| 4,548,157 | 10/1985 | Hevoyan | . |
| 5,135,496 | 8/1992 | Vetter et al. | 604/111 |
| 5,280,876 | 1/1994 | Atkins | 604/905 X |
| 5,501,676 | 3/1996 | Niedospial et al. | 604/283 |
| 5,554,134 | 9/1996 | Bonnichsen | 604/240 |

*Primary Examiner*—Michael Buiz
*Assistant Examiner*—A. T. Nguyen
*Attorney, Agent, or Firm*—Neal D. Marcus

[57] ABSTRACT

The injection molded luer cap of the present invention includes a stiff body having a circumferential sleeve extending downward from the body. The sleeve has an inner circumferential surface for sealingly fitting over the exterior surface of the fitment. A solid stem extends downward concentrically within the sleeve. The stem has an outside surface for a slip fit within the bore of the fitment and supports the male luer fitment during heat sterilization.

23 Claims, 1 Drawing Sheet

LUER CAP FOR TERMINALLY STERILIZED SYRINGE

This application is a continuation of Ser. No. 08/496,990, filed Jun. 30, 1995 now abandoned.

TECHNICAL FIELD

The present invention relates generally to a removable luer cap for a syringe of the type having a male luer fitment and more particularly, to a removable thermoplastic luer cap for such a syringe that allows the sealed syringe to be heat sterilized without detriment to the sealing components.

BACKGROUND OF THE INVENTION

Today's healthcare practitioner is usually provided with medical devices that are ready to use since the devices are typically sterilized during manufacture. This is particularly true of syringes that are used to administer parenteral drugs and other medical solutions.

A syringe typically includes a glass or plastic barrel having a substantially closed end and an opposite open end. The open end is sealed by a slidable piston plunger. The substantially closed end of the syringe has a dispensing port communicating with a male luer fitment, for dispensing the contents of the syringe. The syringe as manufactured may be prefilled with a liquid, part-filled with a lyophilized powder, or empty, for example. A removable end cover, such as a luer cap is placed over the luer fitment during manufacture so as to seal the contents within the barrel. Thus, the end cap remains sealingly in place from manufacture until the syringe is used.

Manufacture also commonly includes "terminal sterilization" of the assembled and sealed syringe. The sterilized syringe is then packaged for later use. Terminal sterilization ensures that the contents of the syringe, as well as the individual syringe elements are provided in a sterile condition at the point of use.

Terminally sterilizing a syringe is usually accomplished with pressurized steam in an autoclave. However, the heat and pressure generated in the autoclave can have an adverse effect on the syringe. For example, vapor pressure and thermal expansion of the contents in a prefilled syringe can cause the syringe sealing members, such as the end cap, to blow out. Additionally, if the barrel or other elements of the syringe are manufactured from plastic, the heat and pressure generated for sterilization can deform these members and inhibit their performance during use.

Typically, the slidable piston plunger is made from a resilient material such as rubber or an elastomer so as to slidably maintain frictional sealing contact with the inside of the barrel as the syringe contents are being delivered. Additionally, the rubber or elastomer plunger can sealingly accommodate any expansion or shrinking of the barrel dimensions due to the heat of sterilization. Thus sterile sealing is maintained during the sterilization process and afterward.

Up until the present invention, the removable luer cap has also conveniently been made of the same rubber or elastomeric material as the slidable piston plunger. Thus, the currently known resilient luer cap will not creep and consequently will not leak due to the heat of sterilization. The currently known resilient luer cap can also sealingly accommodate the dimensional changes of the luer fitment during and after sterilization.

However, the current known luer cap must be manually removed by the healthcare practitioner before the syringe can be used to deliver a medical solution. The resiliency and high frictional coefficient are advantages of the rubber and elastomeric material when they are used to form the sliding piston plunger. However, those same properties are disadvantages when the resilient material is used as a removable luer cap.

In some emergency situations, it maybe difficult for a healthcare provider to quickly remove the resilient rubber or elastomeric luer cap from the dispensing end of the syringe. Furthermore, a part made of soft, resilient material such as rubber or an elastomer tends to be difficult to position by machine in a high speed automated production line. Thus, the currently known resilient luer cap is hard to get on and hard to get off.

There have been previous unsuccessful attempts to manufacture luer caps of stiff or hard thermoplastic material. However, in the presently known configurations similar to configurations used for the rubber or elastomeric materials, the thermoplastic parts can not consistently maintain acceptable sealing and sterility integrity after being subjected to a heat sterilizing process.

Therefore, it is desirable to provide a new configuration for a thermoplastic luer cap that is readily manufactured, readily assembled by machine to the syringe barrel, and readily removed by the healthcare user, while at all times maintaining the sterility and seal integrity of the syringe.

SUMMARY OF THE INVENTION

The present invention provides a removable, injection molded thermoplastic luer cap for a male luer fitment at the dispensing end of a syringe. The thermoplastic luer cap includes a body made of a rigid or stiff material and has a circumferential sleeve extending downward from the body. The sleeve has an inner circumferential surface for sealingly fitting over the exterior surface of the extending male luer fitment. A solid stem extends downward concentrically within the sleeve. The stem has an outside surface for a tight slip fit within the center bore or fluid passageway of the male luer fitment. The tight fit supports the inside of the male luer fitment during heat sterilization so that the outside of the male luer fitment doesn't shrink away from sealing contact with the luer cap.

Additionally, the molded body includes a plug portion such as a finger grip. The finger grip extends from the luer cap body opposite to the sleeve and stem so as to facilitate ready removal of the cap by a healthcare provider.

Other features and advantages of the present drug packaging, mixing, and delivery system will be become readily apparent from the following detailed description, the accompanying drawings, and the appended claims.

DETAILED DESCRIPTION

Figure 1:
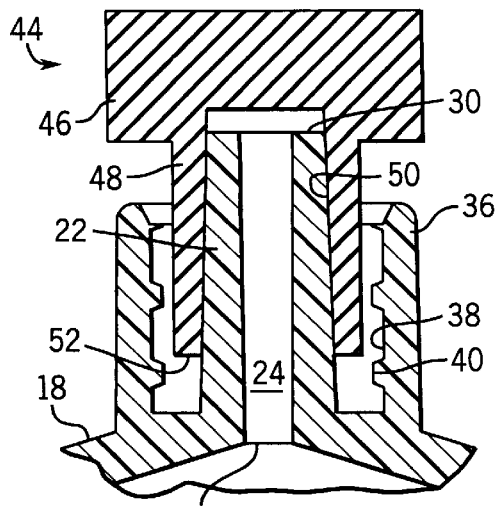
FIG. 1 is a cross-sectional view illustrating the configuration of a resilient luer cap similar to those currently used with a syringe having a male luer dispensing fitment.

While the present invention is susceptible of embodiment in various forms, there is shown in the drawings and will hereinafter be described a presently preferred embodiment, with the understanding the present disclosure is to be considered as an exemplification of the invention, and is not intended to limit the invention to the specific embodiment illustrated.

Figure 2:
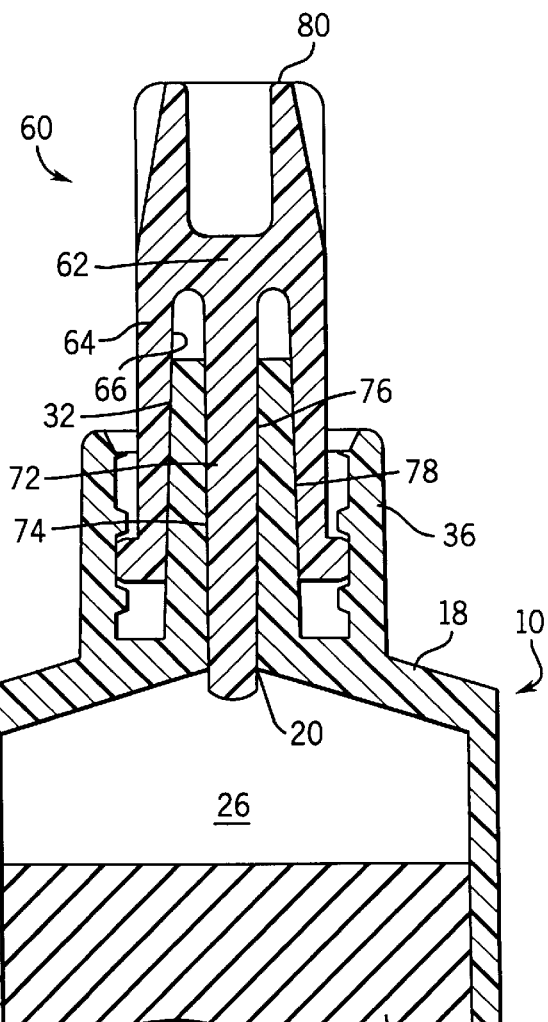
FIG. 2 is a cross-sectional view illustrating a stiff thermoplastic luer cap according to a first embodiment of the present invention for a syringe having a male luer dispensing fitment.

With reference to FIGS. 1 and 2, a typical medical syringe 10 in current use today includes a cylindrical plastic syringe barrel 12 having an open rear end sealed by a slidable piston plunger 14. The barrel has a forward end that is substantially closed by a frontwall 18 having a central dispensing port 20. With reference now to FIG. 1, a frontwall 18 and dispensing port 20 at the forward end of a typical plastic syringe in current use are illustrated. The dispensing port 20 is integrally connected to a male luer fitment 22 which extends forward from the frontwall of the syringe barrel. The male luer fitment is generally tubular and is formed with a center bore or central fluid passageway 24 extending from the enclosed chamber 26 within the barrel to the forward tip 30 of the male luer fitment. The outside surface 32 of the male luer fitment is tapered along the extending length to provide a surface sealingly mateable with the inner tapered surface of a female luer connector. For example, the female luer connector may be in the hub of a sharp needle assembly (not illustrated). The tapered male luer fitment 22 establishes a seat for and seals with the female luer hub.

Preferably the frontwall also has an annular collar 36 radially outward from and extending concentrically with the male luer fitment 22. The collar does not extend longitudinally as far forward as the tip 30 of the luer fitment. The inner face 38 of the collar is formed with internal threads 40 for cooperation with at least one laterally protruding lug portion on an outer radial edge of the female luer connector. Thus, the above described luer and lock structure firmly secures a female luer connector to the male luer fitment 22 of the syringe in a fluid-tight fit.

Currently, during manufacture and prior to use, a removable resilient luer cap 44 is positioned on the male luer fitment 22 so as to seal the dispensing port 20. The luer cap may be formed of any suitable resilient material such as rubber, elastomer, or the like. The luer cap includes a head portion 46 which is larger in diameter than the annular collar 36. A smaller circumferential sleeve portion 48 extends integrally downward from the head portion. The circumferential sleeve 48 has a tapering inside surface 50 so as to fit sealingly over the oppositely tapering male luer fitment 22. The circumferential sleeve 48 has a predetermined minimum diameter so that the tip 30 of the luer fitment does not contact the head portion 46 at the base of the sleeve 48. The extending end 52 of the circumferential sleeve 48 also does not contact the frontwall 18.

An effective seal is established at the tapering interface of the outside surface 32 of the male luer fitment 22 and the inside surface 50 of the circumferential sleeve 48. Minimum and maximum tapering tolerances insure that the male and female luer surfaces are in sealing contact. Sealing contact is maintained because as the diameter of the male luer fitment 22 shrinks and collapses during the heat cycle, the resilient circumferential sleeve portion 48 inherently takes up the diameter difference to preserve the integrity of the seal.

One disadvantage of using a resilient material, such as rubber or elastomer, for the end cap 44 is that a small part or piece formed from a resilient material is difficult for an automated assembly machine to handle and correctly apply at high speeds. Another drawback of the resilient material end cap is that the relative coefficient of friction between the material of the resilient cap 44 and the hard thermoplastic material of the syringe luer fitment 22 is high. The resilient luer cap 44 may inadvertently frictionally stick to the male luer fitment 22 when pulled or twisted, thus making removal of the luer cap more difficult. Also the resilient material may experience a weak heat induced bond to the syringe luer fitment during the heat cycle, which can increase the initial resistance to separation of the luer cap from the luer fitment.

Therefore, simply substituting a thermoplastic material for the resilient material with the same luer cap configuration will not necessarily result in a sealed syringe able to undergo autoclaving. With the application of heat, a thermoplastic male luer fitment 22 tends to collapse or shrink and pull away from the circumferential sleeve 48 of the end cap. Also, the male luer fitment 22 and/or the circumferential sleeve 48 of the end cap may warp due to the heat of sterilization which would compromise the integrity of the mated luer sealing surfaces.

Referring now to FIG. 2, a stiff luer cap 60 according to the present invention is illustrated. The newly configured luer cap 60 is preferably injection molded from a suitable plastic such as a medical grade polypropylene or polyethylene. The stiff luer cap body 62 has a circumferential sleeve 64 extending downward from the body. The sleeve has an inner circumferential surface 66 for sealingly fitting over the exterior surface 32 of the male luer fitment 22.

Figure 3:
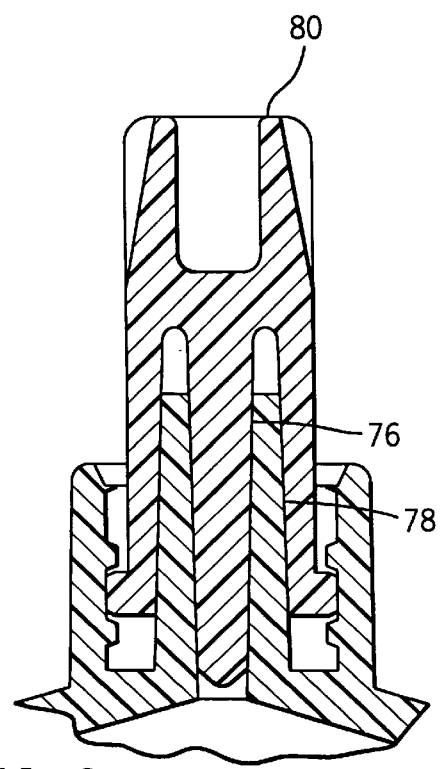
FIG. 3 is a cross-sectional view illustrating another thermoplastic luer cap according to a second embodiment of the present invention for a syringe having a modified male luer dispensing fitment.

A solid stem 72 extends downward concentrically within the circumferential sleeve 44. The stem has an outside diameter surface 74 for a slip fit within the center fluid passageway 24 of the male luer fitment 22. The inside surface of the central fluid passageway 24 and the outside surface of the stem 74 may be straight as illustrated in FIG. 2. Alternatively, the inside central passageway surface 76 and the outside stem surface 78 may each have a reverse taper as illustrated in FIG. 3. In either embodiment, the central stem 72 supports the inside of the extended male luer fitment 22 during the sterilization heat cycle so as to reduce heat induced leakage.

The solid stem 72 extends the complete length of the center sleeve passageway 24, and preferably extends into the syringe chamber 26 as illustrated in FIG. 2 to prevent occlusion of the dispensing outlet 20 by a drug lyophilized in the barrel, for example.

A plug portion 80 that can be easily gripped extends from the luer cap body 62 opposite to the sleeve 64 and stem 72 so as to provide a finger grip for readily disengaging the luer cap 60 from the syringe.

Thus a new configuration for a thermoplastic luer cap that is readily manufactured by injection molding, readily assembled by automated machinery to the syringe barrel, and readily removed by the healthcare user during emergencies has been provided. Furthermore the new luer cap continues at all times to maintaining the sterility and seal integrity of the syringe.

From the foregoing, it will be observed that numerous modifications and variations can be effected without departing from the true spirit and scope of the novel concept of the present invention. The present disclosure is to be understood broadly and no limitation with respect to the specific embodiment herein is intended or should be inferred. The disclosure is intended to cover, by the appended claims, all such modifications as falls within the scope of the claims.

What is claimed is:

1. An assembly including a medical syringe and a removable cap for the medical syringe, said syringe including a barrel having a hollow chamber, an open first end communicating with said chamber for receiving a slidable piston plunger, a second end for dispensing medicament and a luer fitment extending from said second end having a longitudinally extending cylindrically tapering exterior surface and an inner surface defining a center bore which extends from said chamber through said fitment, the cap comprising:

a body portion formed of a stiff material and having a circumferential sleeve extending downward from the body portion, the sleeve having a tapering inner circumferential surface for sealingly fitting over the tapering exterior surface of the fitment; and means extending downwardly from said body portion within said sleeve for supporting said luer fitment during heat sterilization to minimize deformation of said fitment and to prevent said cap from sealing to said syringe.

2. The assembly of claim 1 wherein said means for supporting includes a stem extending downward from said body portion, concentrically within the sleeve, the stem having an outside surface for a slip fit within the bore of the fitment.

3. The assembly of claim 2 wherein said stem extends beyond the length of said fitment into said chamber of said barrel.

4. The assembly of claim 2 wherein said stem is non-resilient and solid, extending substantially the length of the fitment and substantially across the cross-sectional area defining said bore.

5. The assembly of claim 4 wherein said inner surface defining the center bore and the outside surface of the stem each have a complimentary reverse taper.

6. The assembly of claim 2 wherein the cap further comprises a grippable portion extending from the body portion opposite to the sleeve and stem for manual manipulation.

7. The assembly of claim 1 wherein said syringe further including a concentric annular collar which extends from said second end of said barrel and surrounds the fitment, said collar has an interior surface with threads and said cap has at least one radial lug for threadingly engaging said threads of said interior surface of said collar.

8. An assembly including a syringe and a cap for said syringe, said syringe having a barrel with a hollow chamber, an open first end communicating with said chamber for receiving a slidable piston plunger and a second end for dispensing medicament and a male luer fitment extending from said second end having a longitudinally extending cylindrically tapering exterior surface and an inner surface defining a center bore which extends from said chamber through said fitment, the cap comprising:

a stiff body portion having a circumferential sleeve extending downward from the body portion, the sleeve having a tapering inner circumferential surface for sealingly fitting over the exterior surface of the male luer fitment; and means extending from said body portion for supporting said luer fitment during heat sterilization to minimize deformation thereof and to prevent said cap from sealing to said syringe, said means for supporting includes a solid non-resilient stem extending downward from said body portion, concentrically within the sleeve, the stem having an outside surface for providing a slip fit within the bore and for providing support within the center bore of the fitment to resist heat distortion.

9. The assembly of claim 8 wherein said the stem extends beyond the length of said fitment into said chamber of said barrel.

10. The assembly of claim 8 wherein said stem extends substantially the length of said fitment and substantially across the cross sectional area defining said bore.

11. The assembly of claim 8 wherein said inner surface defining the center bore and the outside surface of the stem each have a complimentary reverse taper.

12. The assembly of claim 8 wherein said syringe further including a concentric annular collar which extends from said second end of said barrel and surrounds the fitment, said collar has an interior surface with threads and said cap has at least one radial lug for threadingly engaging said threads of said interior surface of said collar mates with a cooperative fitment that has at least one radial lug for threadingly engaging the collar threads.

13. A assembly having a medical syringe and a removable cap for said syringe, said syringe including:

a barrel having a hollow chamber, an open first end communicating with said chamber for receiving a slidable piston plunger and a second end for dispensing medicament and a luer fitment extending from said second end having a longitudinally extending cylindrically tapering exterior surface and an inner surface defining a center bore which extends from said chamber through said fitment, the cap comprising:

a body portion formed of a stiff material and having a circumferential sleeve extending downward from the body portion, the sleeve having a tapering inner circumferential surface for sealingly fitting over the tapering exterior surface of the fitment; and means extending from said body portion within said sleeve for supporting said luer fitment during heat sterilization to minimize deformation thereof and to prevent said cap from sealing to said syringe, said means for supporting including a solid non-resilient stem extending downward from said body portion, concentrically within the sleeve, the stem substantially the length of said fitment and substantially across the cross-sectional area defining the bore for providing support within the center of the fitment to resist distortion, said stem extending beyond the length of said fitment into said chamber of said barrel, said stem having an outside surface for providing a slip fit within the bore and for providing support within the center bore of the fitment to resist heat distortion.

14. An assembly including a medical syringe and a removable cap for the medical syringe, said syringe including a barrel having a hollow chamber, an open first end communicating with said chamber for receiving a slidable piston plunger, a second end for dispensing medicament and a luer fitment extending from said second end having a longitudinally extending cylindrically tapering an exterior surface and an inner surface defining a center bore which extends ending said chamber through said fitment, said inner bore having a diameter, the cap comprising:

a body portion having a circumferential sleeve extending downward from the body portion, the sleeve having a tapering inner circumferential surface for sealingly fitting over the tapering exterior surface of the fitment; and means extending downwardly from said body portion within said sleeve for maintaining the size of said diameter of said bore of said luer fitment during heat sterilization and for preventing said cap from sealing to said syringe.

15. The assembly of claim 14 wherein said means for maintaining includes a stem extending downward from said body portion, concentrically within the sleeve, the stem having an outside surface for a slip fit within the bore of the fitment.

16. The assembly of claim 15 wherein the cap further comprises a grippable portion extending from the body portion opposite to the sleeve and stem for manual manipulation.

17. The assembly of claim 15 wherein said stem extends beyond the length of said fitment into said chamber of said barrel.

18. The assembly of claim 17 wherein said stem is non-resilient and solid, extending substantially across the cross-sectional area defining said bore.

19. The assembly of claim 18 wherein said inner surface defining the center bore and the outside surface of the stem each have a complimentary reverse taper.

20. The assembly of claim 14 wherein said syringe further including a concentric annular collar which extends from said second end of said barrel and surrounds the fitment, said collar has an interior surface with threads and said cap has at least one radial lug for threadingly engaging said threads of said interior surface of said collar.

21. A assembly having a medical syringe and a removable cap for said syringe, said syringe including:

a barrel having a hollow chamber, an open first end communicating with said chamber for receiving a slidable piston plunger and a second end for dispensing medicament and a luer fitment extending from said second end having a longitudinally extending cylindrically tapering exterior surface and an inner surface defining a center bore which extends from said chamber through said fitment, the cap comprising:

a body portion formed of a stiff material and having a circumferential sleeve extending downward from the body portion, the sleeve having a tapering inner circumferential surface for sealingly fitting over the tapering exterior surface of the fitment; and a solid non-resilient stem extending downward from said body portion, concentrically within the sleeve, the stem having an outside surface for providing a slip fit within the bore and for providing support within the center bore of the fitment and for preventing said cap from sealing to said syringe during heat sterilization of said assembly.

22. The assembly of claim 21 wherein the stem maintains the diameter of the bore by extending substantially the length of said fitment and substantially across the cross-sectional area defining the bore.

23. The assembly of claim 22 wherein the stem extends beyond the length of said fitment into said chamber of said barrel.

* * * * *